(12) United States Patent
Alruhaimi

(10) Patent No.: US 12,076,212 B1
(45) Date of Patent: Sep. 3, 2024

(54) INTERNAL SINUS LIFTING DRILL SET

(71) Applicant: KING SAUD UNIVERSITY, Riyadh (SA)

(72) Inventor: Khalid Abdullah Alruhaimi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/444,853

(22) Filed: Feb. 19, 2024

(51) Int. Cl.
*A61C 8/00* (2006.01)
*A61B 17/16* (2006.01)

(52) U.S. Cl.
CPC ........ *A61C 8/0092* (2013.01); *A61B 17/1615* (2013.01); *A61B 17/1688* (2013.01); *A61C 8/0037* (2013.01); *A61C 2008/0046* (2013.01)

(58) Field of Classification Search
CPC ....... A61C 1/084; A61C 1/085; A61C 8/0092; A61C 8/009; A61C 8/0089; A61C 8/0037; A61C 2008/0046; A61B 17/1616; A61B 17/1615
See application file for complete search history.

(56) References Cited

U.S. PATENT DOCUMENTS

| 9,498,308 B1 | 11/2016 | Krastev |
| 9,757,215 B2 | 9/2017 | Song |
| 2006/0121415 A1* | 6/2006 | Anitua Aldecoa ... A61C 8/0089 433/165 |
| 2013/0150857 A1* | 6/2013 | Better ................. A61C 8/0092 606/80 |
| 2016/0128810 A1* | 5/2016 | Fostick ............. A61B 5/02233 703/1 |
| 2020/0276000 A1* | 9/2020 | Kim ..................... A61C 8/0092 |

FOREIGN PATENT DOCUMENTS

| CN | 110811756 A | 2/2020 |
| KR | 20120014373 A | 2/2012 |
| KR | 20180104352 A | * 9/2018 ............... A61C 1/08 |
| KR | 20210010024 A | 1/2021 |

OTHER PUBLICATIONS

Attanasio, et al., "Flapless Cone Beam Computed Tomography-Guided Implant Surgery with Contextual Transcrestal Sinus Lift Augmentation Using New Bone Compactor Tools" Case Reports in Dentistry 2020:8873234 (2020).

* cited by examiner

*Primary Examiner* — Yogesh P Patel
(74) *Attorney, Agent, or Firm* — Nath, Goldberg & Meyer; Joshua B. Goldberg

(57) ABSTRACT

A system and method is provided for performing internal maxillary sinus lift procedures where the system and method employs a set of sequentially deployed surgical drill bits to be used in conjunction with a dental implant surgical kit for performing internal maxillary sinus lift procedures in the dental implant surgical situations where the sub-antral bone height is not adequate to host an implant.

1 Claim, 4 Drawing Sheets

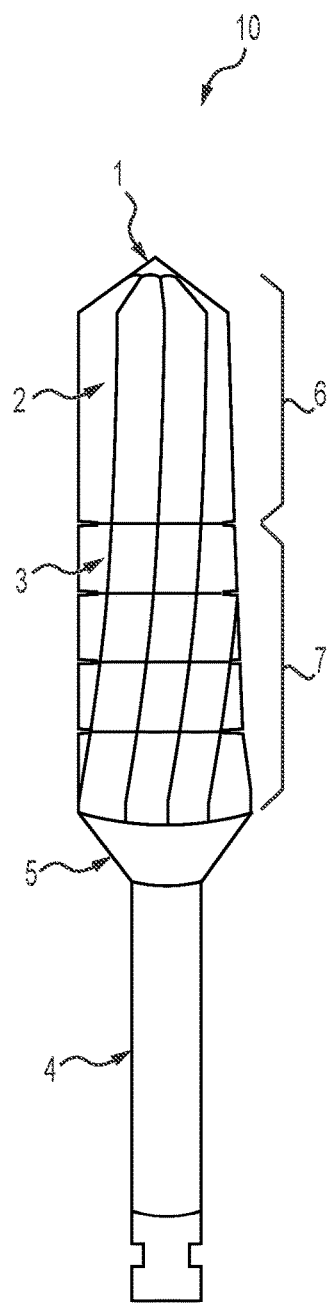
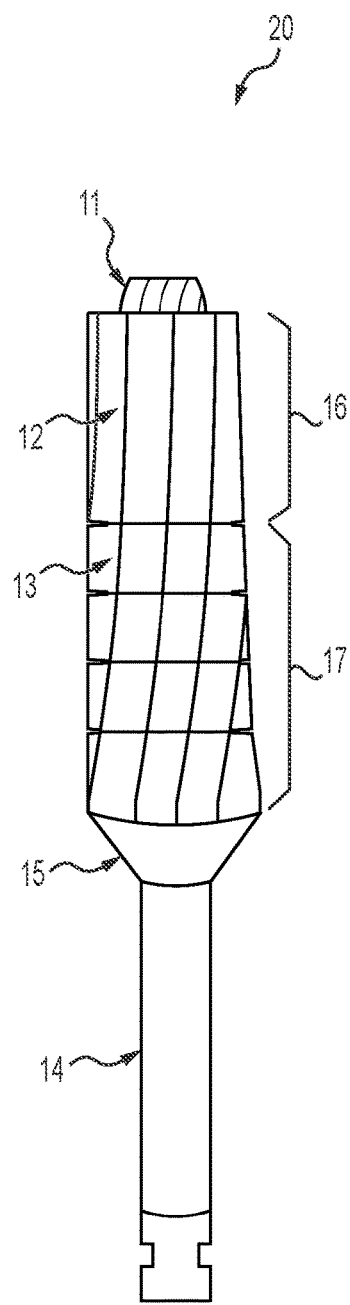
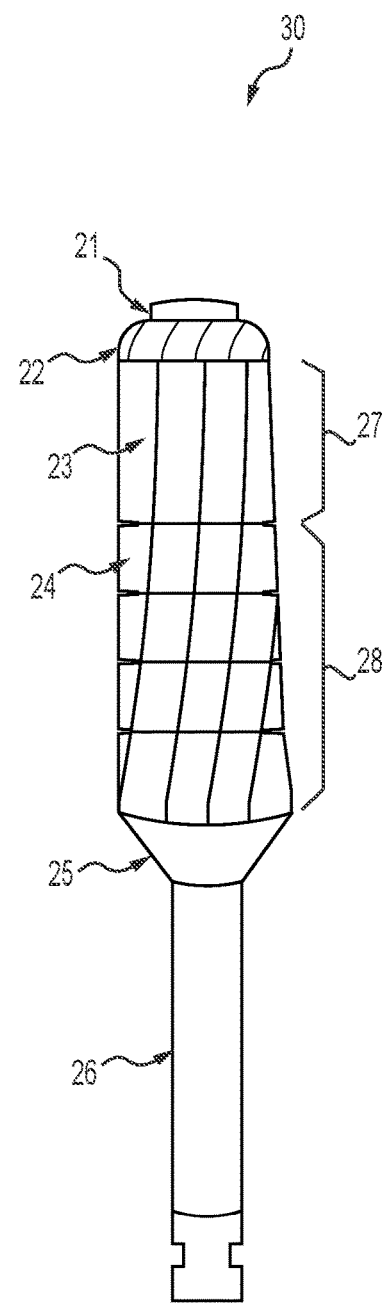
FIG. 1A  FIG. 1B  FIG. 1C

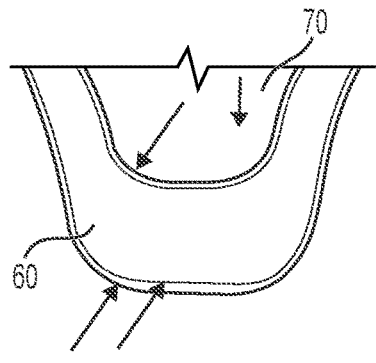
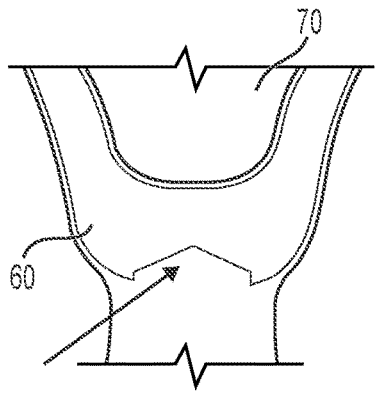
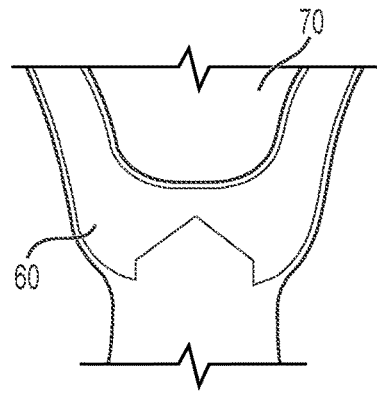
FIG. 4A  FIG. 4B  FIG. 4C
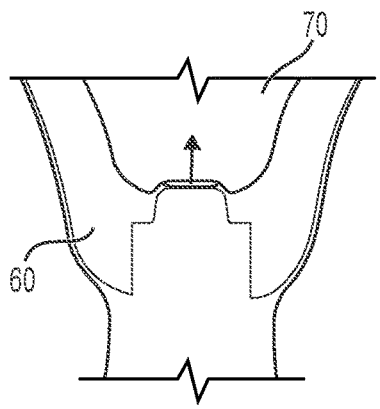
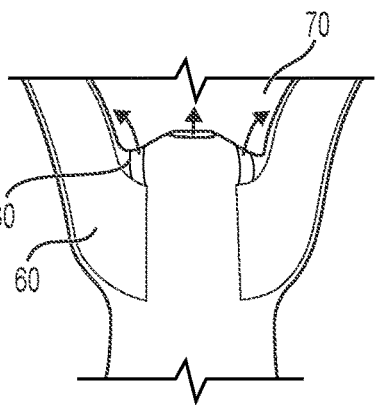
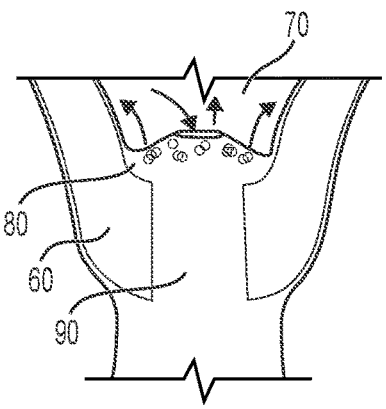
FIG. 4D  FIG. 4E  FIG. 4F
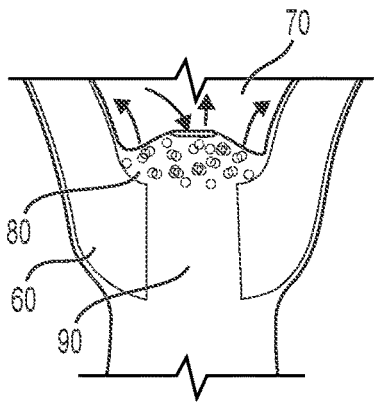
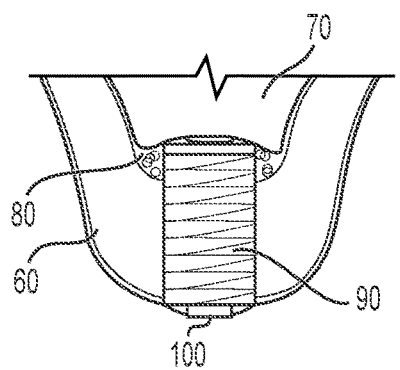
FIG. 4G  FIG. 4H

INTERNAL SINUS LIFTING DRILL SET

BACKGROUND

1. Field

The present disclosure relates to a set of serial surgical drill bits to be used in conjunction with a dental implant surgical kit for performing internal maxillary sinus lift procedures in the dental implant surgical situations where the sub-antral bone height is not adequate to host an implant and an associated method.

2. Description of the Related Art

The sinus lift procedure is a surgical procedure used in dental implant surgery to increase thickness of the sub-antral maxillary segment to host an implant with appropriate width and length. This procedure is widely used in circumstances where the sub-antral maxillary segment is very short and is not able to host a dental implant suitably and would perhaps invade the sinus membrane and perforate the maxillary sinus if the sinus membrane is not carefully elevated enough according to implant length.

The conventional implant surgical methods used for maxillary sinus lifting have been categorized in two types and each method uses a different approach to the sinus. The first method approaches the sinus laterally through a lateral maxillary wall after lifting the mucoperiosteal tissue at the buccal vestibule. A lateral bone window is created through drilling into the lateral maxillary bony wall to expose the sinus membrane directly. The sinus membrane is then lifted to increase the sub-antral bone height and implant is directly placed through a drill hole from the crestal direction and with a subsequent bone graft the newly created sub-antral space is filled. The second method approaches the sinus vertically through an drilling implant hole via the alveolar crest. Accordingly, the sinus membrane is lifted indirectly with cylindrical osteotomes through the implant hole. The first lateral approach has the numerous disadvantages in that the surgery itself is difficult to perform, consumes longer surgical time, requires a larger surgical site to access the sinus, requires a more extensive mucoperiosteal flap exposure, and lastly, further necessitates the additional harvesting of more bone to reach to the sinus membrane. Therefore, more post-operative edema, pain, and discomfort may occur after the surgery.

In contrast, the original technique of the vertical internal lifting of the sinus mucosa uses different sizes of cylindrical osteotomes through the crestal bone hole and lift the membrane by knocking the remaining spongy bone near the sinus with an osteotome in order to break it and push it upwards to hence lift the sinus membrane. The process of knocking causes palpable impacts and jarring noise to the patient and makes a patient feel pain and fear. Therefore, this process disadvantageously puts the patient in a heightened state of anxiety and elevates the patient's discomfort. Additionally, there is higher likelihood of sinus membrane perforation with the use of this knocking procedure especially if it is done with an unskilled operator.

Therefore, there is a need for the use of a set of serial drill bits with different configurations and sizes in order to drill an implant hole in the sub-antral bone segment through a vertical approach via the alveolar crest according to the selected and/or desired implant size. The invention has the advantages over others in that it offers safe, easy surgery, comfortable surgery to the patient and the surgeon with a shorter surgical time.

SUMMARY

The invention allows antral mucous membrane to be easily and safely lifted through the implant hole without being damaged. According to the present invention, a set of surgical drill bits are designed to serve for this purpose. Each drill in the set includes a universal connection portion formed at the end of the shank of the drill bit to be connected with a motor driving device such as a hand-held drill, and a cutting portion formed in the upper part of the bits which comes in different shapes and sizes to harvest bone through drilling vertically in the available alveolar crestal bone in stages to arrive a drilled out implant hole suitable for the desired implant size. The sub-antral bone bed below the sinus membrane is easily and safely ground and broken with the specifically designed surgical drill bits and the thus the sinus membrane is lifted upwards without the risk of perforation. Further, the required implant length can be easily achieved such that the dental implant can be safely placed therein afterwards with more convenience and less invasion while providing more comfort to the patient.

The disclosed tools for drilling bone tissue are particularly suitable for use when performing a sinus lift in dental implant surgery. The drill bits as shown in the attached figures of 1A-1C consist of three sequenced configurations and serrated for depth identification. The burr set should be used gradually to lead to a safe and successful surgery. This means that each drill bit structure should follow in use to the next accordingly. That is the procedure would start with the drill bit (10) of FIG. 1A, followed by the drill bit (20) of FIG. 1B, and finally terminating with the implementation of the drill bit (30) of FIG. 1C.

Each bit shape come in different sizes according to the selected implant size.

The sub-antral bone height and width is first determined with a cone beam computed tomography (CBT).

Through the sequential use of drills bits, the sub-antral bone is drilled and harvested to elevate sinus membrane through the crestal approach. Surgeons can choose the type of surgical procedure from between the flapless technique or the elevating the crestal mucoperiosteal tissue depending on his/her experience and morphology of the crestal bone.

Respective groups of burrs are composed of different diameters. However, within each group, a set of preferably three drill bits is composed of the same diameter.

These and other features of the present subject matter will become readily apparent upon further review of the following specification.

BRIEF DESCRIPTION OF THE DRAWINGS

FIGS. 1A-1C are a diagram showing the perspective view of three types of the implant drills bits in a first group according to the present invention.

FIGS. 4A-4H are a diagram showing the various stages of the implant hole preparation by drills sets of the present invention at the sub-antral crestal bone.

Similar reference characters denote corresponding features consistently throughout the attached drawings.

DETAILED DESCRIPTION OF EMBODIMENTS

Figures 2A, 2B:
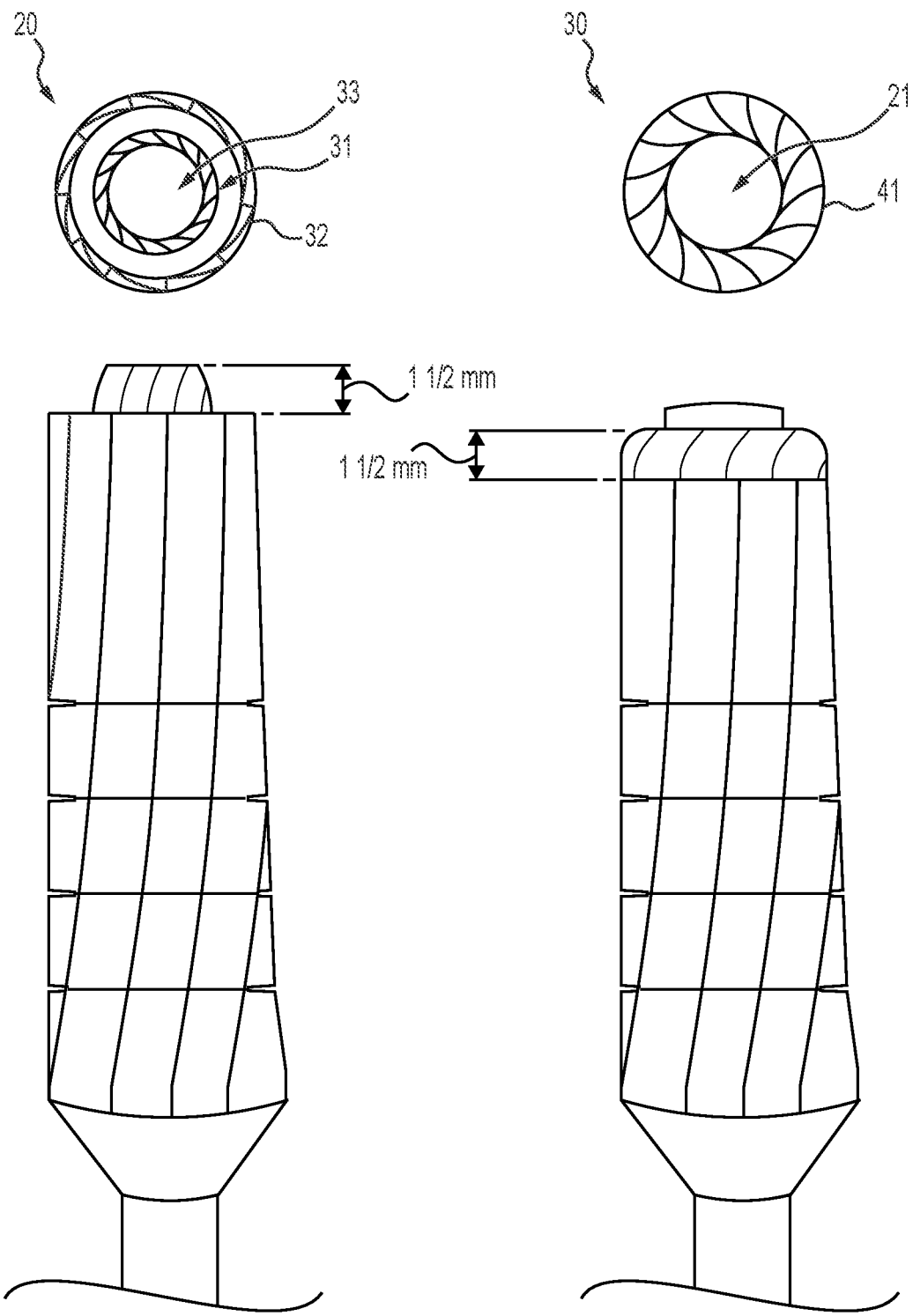
FIGS. 2A-2B are a diagram showing the front and top views of the second and third drill bits of the first group according to the present invention.

The following detailed description is merely exemplary in nature and is not intended to limit the described embodiments or the application and uses of the described embodiments. Any implementation described herein with the words "exemplary" or "illustrative" is not necessarily construed as preferred or advantageous over other implementations. All of the implementations described below are exemplary implementations provided to enable persons skilled in the art to make or use the embodiments of the disclosure and are not intended to limit the scope of the disclosure, which is defined by the claims. For the purposes of the description herein, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed therein are not to be considered as limiting, unless the claims expressly state otherwise.

As shown in FIGS. 1A-1C, the first group of comprises a set of preferably three drill bits (10), (20), (30) which are used in sequence to create a bone hole according to the selected implant size. The drill bits disclosed herein are each constituted of several interconnected components: the tip, the head, the crown, and the shank. The first drill bit (10) of the first group includes a pointed tip (1). Directly below the pointed tip (1) is the head portion (6), (7) of the first drill bit which contains contain sharp teethed edges (2), (3) at the circumference running in an oblique direction along the drill bit length. The crown (5) of the head portion (6), (7) of the first drill bit connects to a drill bit shank (4). The pointed tip (1) and the sharp teethed edges (2), (3) of the head portion (6), (7) drill a hole in the sub-antral bone segment and cut along the segment's sides in a sequence of diameters (example for implant sized at 4 mm they drill in sequence and not limited to 2 mm, 2.5 mm, 3 mm, and 3.5 mm) to form the required implant drill width. The first group of the drill bit set as shown in FIGS. 1A-1C corresponds fashioning a hole of 2 mm. Accordingly, additional groups of the drill bit sets would be sized for holes of 2.5 mm, 3 mm, and 3.5 mm, respectively. The drilling height is measured according to the sub-antral bone thickness as shown through CBT and drilling should stop at least 2 mm from the floor of the sinus cavity. The speed of drilling is according to the conventional implant protocol and the quality of the crestal bone (soft, hard, hollow, etc.)

As shown in FIGS. 1B and 2A, the second drill bit (20) of the first group (10), (20), (30) is deployed after creating the selected bone hole width with the first drill bit (10) and is used to drill the center of the remaining sub-antral bone segment at the upper portion of the bone hole (the remaining 2 mm sub-antral bone segment), while maintaining the hole wall diameter as prepared with the first drill bit (10) of the set. The upper tip portion (11) of this drill bit (20) is configured to be half-spherical in shape while being approximately 1.5-2.0 mm in height and less in diameter by 1.5-2.0 mm than the diameter of head portion (6), (7) of first drill bit used. This second drill bit forms stop shoulders at the circumference of the drill bit tip portion (11) where the formed shoulder surface is flat non-cutting surface sized by approximately 0.75-1.0 mm at each side of circumference of the burr. The circumference (31) of the spherical portion (11) is serrated with oblique cutting teeth (31) to enable further grinding of the center of the sub-antral bone segment while the upper surface of the hemispherical tip portion (11) is constructed to be flat projection (33) to avoid cutting and perforation of the sinus membrane during rotation of the burr. Also shown in FIG. 2A is top down view of the tip (11) and head portion (16), (17) of the second drill bit (20) including the outer circumference (32) of the shallow obliquely serrated teeth (12), (13) that run along the head portion (16), (17) of the second drill bit in the first group. FIG. 1B shows side view of the second drill bit of the group which includes a half-spherical tip (11) portion of the drill bit (20). The head portion (16), (17) of the second drill bit contains contain sharp teethed edges (12), (13) at the circumference running in an oblique direction along the drill bit length. The crown (15) of the head portion (16), (17) of the second drill bit (20) connects to a drill bit shank (14). The sides of the drill bit have shallow obliquely serrated rounded teeth (12), (13) to ease entering through the prepared implant hole without widening the hole diameter or grinding more of the hole walls that were prepared with the first drill bit (10).

It is recommended at this stage to change rotation of the driving motor to rotate counterclockwise in a slow motion (for example 100 rpm). This reverse slow motion of the drill helps to avoid fast penetration of the membrane and further aids in pushing the ground bone slowly towards the sinus cavity to ease elevation of the membrane safely, provides a barrier between the membrane and the head of the drill bit, and adds a bone filling to the raised sinus cavity. The nature of the sinus membrane is rather elastic and if operator advances the drill bit with a slow counterclockwise rotation the operator will feel a shuddering of wobbling of the membrane pushing the drill bit head down away from oscillating membrane. This sensation will alert the operator to thus help prevent penetration the membrane. A 0.75-1.0 mm of the sub-antral bone segment circumference is left after drilling out the center of the remaining sub-antral bone thickness. The hemispherical portion of the tip (11) of the drill bit (20) advances slowly towards the sinus and the feeling of the membrane pumping against the drill bit's head portion can be felt. At the same time the stop shoulders, the clear area in FIG. 2A between circumference of (31) and (32), help prevent the operator from unwanted advancement of the drill as the drill shoulders rotate passively over the remaining unbroken sub-antral bone.

As shown in FIG. 1C, the third drill bit (30) of the first group is shaped similar to the second drill bit (20) but the cutting edges (22) are added above the head portion (27), (28). The smooth non cutting shoulders of the second bit in the first group of are changed here, with the aforementioned several small cutting edges (22) to enable further grinding and breaking the remaining (0.75-1.0 mm) sub-antral bone shoulders, whereas the cutting hemispherical portion (11) in the second set of burrs in the second drill bit are changed here to be a smooth non-cutting protruding tip (21) to avoid membrane tearing during the advancement of drill bit (30) and to help to elevate the sinus membrane more towards the sinus cavity. The sides of this third drill bit also have shallow obliquely serrated rounded teeth (23, 24) to ease entering through the prepared implant hole without widening the hole diameter or grinding more of the hole walls that were prepared with the previous two drill bits. This third drill bit of the first group includes a protruding tip (21) of the drill bit (30). The upper portion (22) of this third drill bit contains contain sharp teethed edges (22), (23), (24) at the circumference. The crown (25) of the head portion (27), (28) of this third drill bit connects to a drill bit shank (26). It is also recommended to use a slow counterclockwise motion with the third drill bit to avoid fast advancement of the drill towards the sinus cavity. FIGS. 2A-2B show how the hemispherical portion (11) of the second drill bit (20) is changed in the third drill bit (30) to be a flat and smooth protruding tip (21) on all sides without cutting teeth as the drill bit in this stage is already advanced inside the sinus cavity after the membrane is lifted initially with second drill bit (20). Note the sides of the shoulder is are beveled with cutting teeth (41) to break the remaining circumference of the sub-antral bone segment towards the sinus cavity during advancement of the drill bit (21). Similarly, the sides of this third drill bit (27), (28) are made with shallow obliquely serrated rounded teeth (23), (24) to ease entering through the prepared implant hole without widening the hole diameter or grinds more of the implant hole walls that are prepared with the first drill bit. The sinus membrane after completion of this phase can be safely raised by 3-4 mm.

Figure 3A:
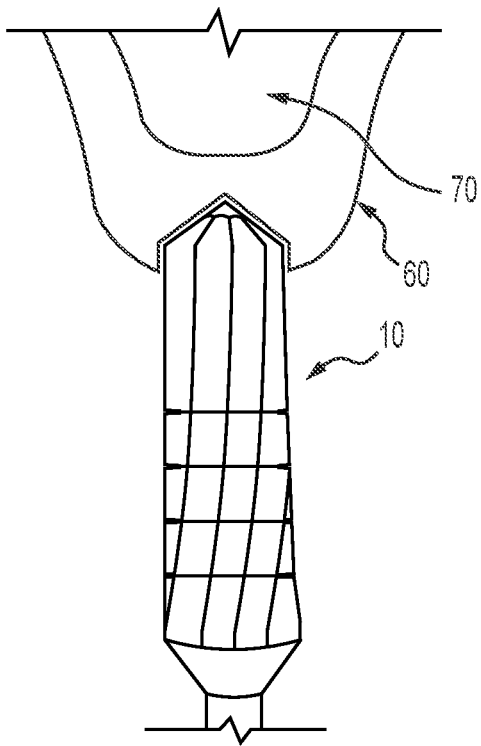
FIGS. 3A-3D are a diagram showing the types of bone hole preparation by the first group of the invention.
Figure 3B:
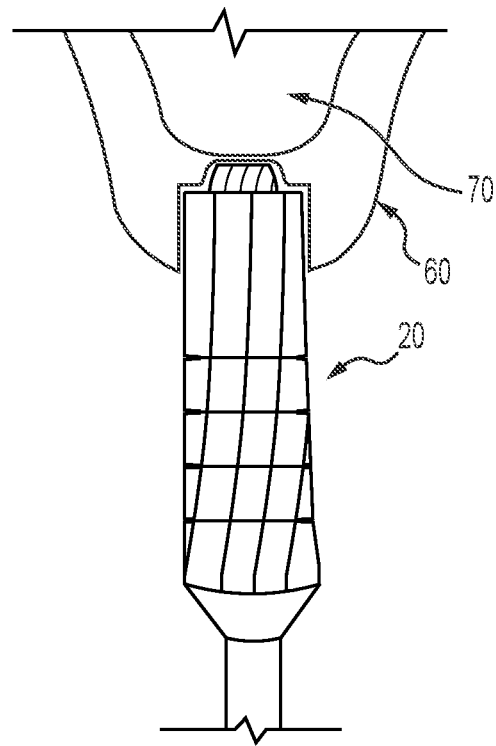
Figure 3C:
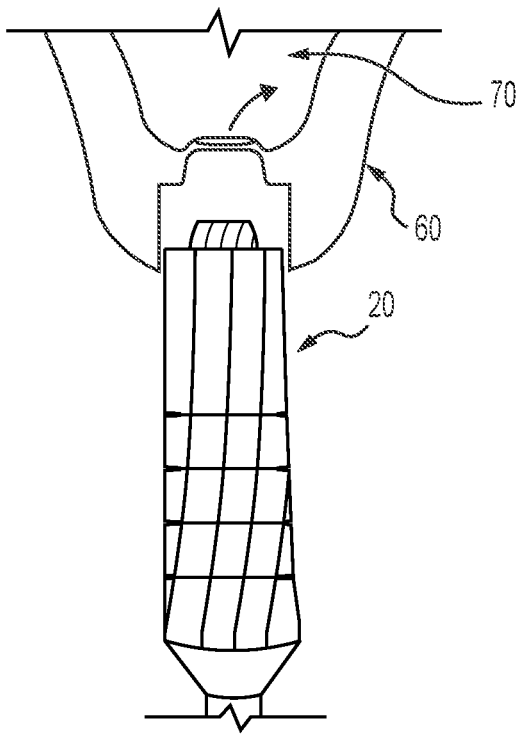
Figure 3D:
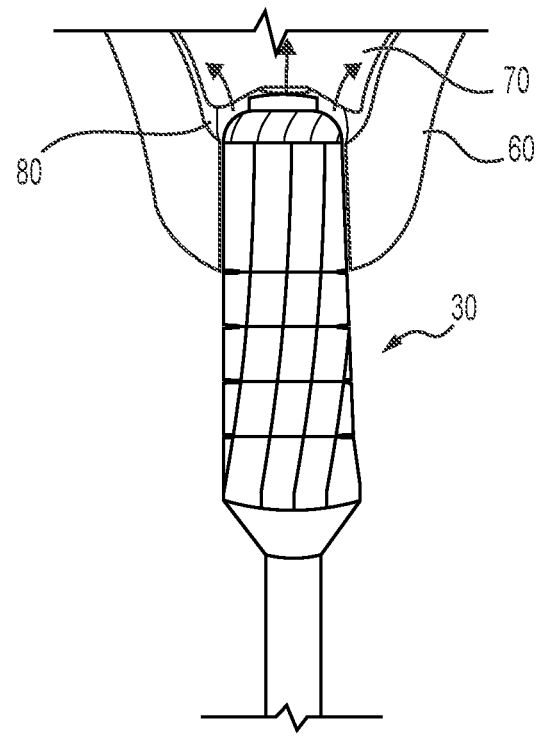

FIGS. 3A-3D show the stages of bone hole preparation in the sub-antral bone using all three drill bits of the first group. In FIG. 3A, the first drill bit (10) is shown penetrating the sub-antral bone (60) and is depicted inside the harvested bone hole at a stop distance 2 mm away from the sub-antral bone segment and separate from the membrane (70). FIGS. 3B-3C show the second drill bit (20) grinding down the center of the remaining sub-antral bone segment and also show the start of membrane elevation (70) leaving shoulders of the bone at the circumference of the upper portion of the sub-antral bone (60). In figure D, the third drill bit (30) completes the breakage of the remaining sub-antral bone (60) shoulders and elevates the sinus membrane (70) safely.

FIGS. 4A-4H show the stages of the implant hole preparation by first group of drill bits at the sub-antral crestal bone (60). FIG. 4A shows a depiction of the surgical site including a longitudinal cross-section of the layers of alveolar crest at the sub-antral region, muco-periosteum, sub-antral alveolar bone, maxillary sinus membrane and sinus cavity, respectively. In FIG. 4B, the first drill bit penetrates the bone made in the sub-antral bone segment (60). In FIG. 4C, the final hole size in the sub-antral bone (60) according to the selected implant size is prepared by the tip (1) to the first drill bit (10). Note the 2 mm sub-antral bone segment (60) is maintained for the following drill bit (20). In FIG. 4D, the center of the sub-antral bone segment (60) is ground by the tip (11) of the second drill bit (20) of the first group. The flat surface of the drill tip projection (11) is advanced to merely touch the sinus membrane (70) and note the shoulders of the second drill bit (20) is stopped from further advancement at the outer circumference of the sub-antral bone segment (60). In FIG. 4E, the outer circumference of the sub-antral bone segment (60) is further broken down and pushed upwards (80) to elevate the sinus membrane (70) safely by the third drill bit (30) of the first group. In FIG. 4F, even more elevation of the membrane (70) is performed by further advancement of the third drill bit (30) towards the sinus cavity. In figure G, even more bone graft granules can fill (80) the created cavity (90) after elevation of the membrane (70) using the third drill bit (30). In figure H, the selected implant (100) is fixed inside the prepared bone hole (90) and the created cavity under the elevated sinus membrane (70).

It is to be understood that the sinus lift method for dental implant and device(s) for lifting a sinus for dental implants is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for lifting a sinus for dental implants by sequentially using a first group of drill bits with a drilling device by an operator, the method comprising:
   connecting a first drill bit to the drilling device and imparting a clockwise rotation to said first drill bit;
   using said first drill bit, said first drill bit having a pointed tip and a circumference of sharp teeth edge running along a length of said first drill bit, drilling into a sub-antral bone segment of a patient and cut along the sub-antral bone's segment's sides to form a required implant width;
   removing said first drill bit from said drilling device;
   connecting a second drill bit to the drilling device and imparting a clockwise rotation to said second drill bit;
   using said second drill bit, said second drill bit having a hemispherical shaped tip with an upper surface comprising a flat projection with a serrated circumference of oblique cutting teeth to further grind a center of the sub-antral bone segment while avoiding cutting and perforating a sinus membrane;
   reversing the clockwise rotation imparted by the drill device to a slow motion counterclockwise rotation to push ground sub-antral bone fragments towards a sinus cavity of the patient to further ease the elevation of the sinus membrane;
   sensing for a shuddering or wobbling of the sinus membrane by the operator;
   removing said first drill bit from said drilling device;
   connecting a third drill bit to the drilling device and imparting a clockwise rotation to said third drill bit;
   using said third drill bit, said third drill bit having a flat protruding tip atop with an upper surface and an upper portion; said upper portion comprising cutting edges to further grinding and breaking of remaining sub-antral bone segment shoulders while avoiding cutting and perforating a sinus membrane and also elevating the sinus membrane;
   reversing the clockwise rotation imparted by the drill device to a slow motion counterclockwise rotation to push ground sub-antral bone fragments towards a sinus cavity of the patient;
   removing said third drill bit from said drilling device; and
   implanting a dental implant within the implant hole.

\* \* \* \* \*